United States Patent
Cai et al.

(10) Patent No.: US 9,835,575 B2
(45) Date of Patent: Dec. 5, 2017

(54) RATIOMETRIC DEVICE

(71) Applicant: ams International AG, Rapperswil (CH)

(72) Inventors: Zeyu Cai, The Hague (NL); Michiel Pertijs, Delft (NL); Robert Hendrikus Margaretha van Veldhoven, Valkenswaard (NL); Kofi Afolabi Anthony Makinwa, Delft (NL)

(73) Assignee: ams International AG, Rapperswil-Jona (CH)

( * ) Notice: Subject to any disclaimer, the term of this patent is extended or adjusted under 35 U.S.C. 154(b) by 374 days.

(21) Appl. No.: 14/516,338

(22) Filed: Oct. 16, 2014

(65) Prior Publication Data
US 2016/0109396 A1 Apr. 21, 2016

(51) Int. Cl.
*G01R 1/38* (2006.01)
*G01N 27/18* (2006.01)
*G01N 25/18* (2006.01)

(52) U.S. Cl.
CPC .............. *G01N 27/18* (2013.01); *G01N 25/18* (2013.01)

(58) Field of Classification Search
CPC ........ G01R 15/02; G01R 15/08; G01R 15/09; G01R 15/125; G01R 15/144; G01R 13/02
See application file for complete search history.

(56) References Cited

U.S. PATENT DOCUMENTS

| | | | | |
|---|---|---|---|---|
| 4,269,061 A | * | 5/1981 | Hatsuno | G01M 3/2815 340/605 |
| 5,685,194 A | * | 11/1997 | McCulloch | G01F 23/246 73/204.11 |
| 5,744,968 A | * | 4/1998 | Czarnocki | G01P 15/131 324/608 |
| 6,118,398 A | * | 9/2000 | Fisher | H03M 1/0653 341/119 |
| 6,279,405 B1 | * | 8/2001 | Clark | G01F 1/363 73/32 R |
| 6,974,934 B2 | * | 12/2005 | Sprock | G01K 1/024 219/483 |

(Continued)

OTHER PUBLICATIONS

Mohan, N. Madhu, et al.; "A Novel Dual-Slope Resistance-to-Digital Converter"; IEEE Transactions on Instrumentation and Measurement, vol. 59, No. 5; pp. 1013,1018 (May 2010).

(Continued)

*Primary Examiner* — Tung X Nguyen
*Assistant Examiner* — Dominic Hawkins
(74) *Attorney, Agent, or Firm* — McDermott Will & Emery LLP

(57) ABSTRACT

One example discloses a ratiometric device, including: a current source having a first current, a second current different from the first current, and a current-select program; a sensor device responsive to a gas and having a sensor-cold temperature T(cold,sens) in response to the first current and a sensor-hot temperature T(hot,sens) in response to the second current; a reference device having a reference-cold temperature T(cold,ref) in response to the first current and a reference-hot temperature T(hot,ref) in response to the second current; and wherein the ratiometric device includes a temperature difference ratio output based on T(cold,sens), T(hot,sens), T(cold,ref) and T(hot,ref).

18 Claims, 8 Drawing Sheets

(56) References Cited

U.S. PATENT DOCUMENTS

| | | | | |
|---|---|---|---|---|
| 7,088,086 B2* | 8/2006 | Ammar | G01K 11/006 250/250 |
| 7,221,141 B2* | 5/2007 | Bills | G01K 11/006 324/95 |
| 7,250,747 B1* | 7/2007 | Ammar | G01J 5/522 324/76.14 |
| 7,401,510 B2* | 7/2008 | Ando | G01F 1/684 73/204.15 |
| 7,667,468 B1* | 2/2010 | Anderson | G01D 5/24 324/676 |
| 8,604,961 B1* | 12/2013 | Bogner | H03M 1/0619 341/118 |
| 2003/0235925 A1* | 12/2003 | Bonne | G01N 33/0063 436/181 |
| 2004/0183516 A1* | 9/2004 | Reischl | G01D 3/0365 324/71.1 |
| 2005/0194959 A1* | 9/2005 | Miller | G01V 3/088 324/67 |
| 2006/0176930 A1* | 8/2006 | Yoo | G01J 1/58 374/121 |
| 2009/0133472 A1 | 5/2009 | Tada et al. | |
| 2009/0277246 A1* | 11/2009 | Ooishi | G01N 27/18 73/25.03 |
| 2010/0079197 A1* | 4/2010 | Ladurner | H03K 17/0822 327/512 |
| 2011/0050435 A1* | 3/2011 | Katayama | G03B 21/16 340/635 |
| 2011/0296910 A1* | 12/2011 | Lopez | G01F 1/6842 73/204.27 |
| 2013/0301680 A1* | 11/2013 | Qiu | G01K 7/01 374/184 |
| 2014/0159678 A1* | 6/2014 | Park | G05F 1/10 323/229 |

OTHER PUBLICATIONS

Mohan, N. Madhu et al; "Analysis of a Sigma—Delta Resistance-to-Digital Converter for Differential Resistive Sensors"; IEEE Transactions on Instrumentation and Measurement, vol. 58, No. 5; pp. 1617,1622 (May 2009).

Owen, Earle W.; "An Integrating Analog-to-Digital Converter for Differential Transducers"; IEEE Transactions on Instrumentation and Measurement, vol. IM-28, No. 3; pp. 216-220, (Sep. 1979).

Rairigh, D., et al; "Baseline Resistance Cancellation Circuit for High Resolution Thiolate-Monolayer-Protected Gold Nanoparticle Vapor Sensor Arrays"; Circuits and Systems, 2008. ISCAS 2008. IEEE International Symposium on; pp. 2002-2005; (May 18-21, 2008).

Anderson, Russel, "Understanding Ratiometric Conversions", Texas Instruments, Application Report SBAA110, Mar. 2004.

Cai, et al., "A Ratiometric Readout Circuit for Thermal-Conductivity-Based Resistive Gas Sensors", Delft University of Technology, NXP Semiconductors; IEEE 2015, 978-1-4673-7472-9/15.

Cai, et al., "An integrated carbon dioxide sensor based on ratiometric thermal-conductivity measurement", Delft University of Technology, NXP Semiconductors; Transducers 2015; IEEE 2015, 978-1-4799-8955-3/15.

Mohan, et al., "A Sigma-Delta Resistance to Digital Converter Suitable for Differential Resistive Sensors" Indian Institute of Technology Madras; IEEE 2008, 1-4244-1541-1/08, Chennai, India.

* cited by examiner

RATIOMETRIC DEVICE

In one example of a steady-state thermal conductivity/resistivity measurement, the accuracy of the measured thermal conductivity usually depends on an accurately measured temperature and well-controlled power dissipation. By Joule heating, when a heated resistor dissipates power (P) within an ambient environment, the generated temperature difference ($\Delta T$) between the heater and the ambient environment is directly proportional to a thermal resistance ($\theta$) between them, as described by equation (1):

$$\Delta T = P \times \theta \qquad (1)$$

This technique can characterize various types of gases and/or parameters that are related to the gas properties. For example, when a suspended hot wire is surrounded by an ambient gas mixture, the gas mixture forms a certain thermal resistance between the hot wire and its ambient, hence resulting in a certain temperature difference between the hot wire and the ambient. Any change in gas composition will change the thermal resistance between the heater and its ambient, which finally results in a slightly different steady-state temperature of the heater.

In order to measure thermal resistance accurately, one prerequisite is that the dissipated power needs to be kept very stable or needs to be measured very accurately. For some gases (e.g. $CO_2$) the stability requirement can be substantial. Temperature measurements, in some embodiments of thermal resistance measurement, are implemented by measuring a (temperature-dependent) electrical resistance of a heater. Three example techniques for measuring such electrical resistance immediately follow.

A first example technique for measuring electrical resistance is performed by measuring a sensor resistor and a reference resistor with same nominal resistance in a dual-slope RDC. This approach however does not take account of the practical mismatch of the nominal resistances within the sensor and reference resistors. In addition, two stable voltage references are also required in order to generate the two polarity currents in the dual-slope converter.

In a second example technique for measuring electrical resistance, a differential resistive sensor incorporating a pair of resistors with inverse characteristics is employed. This category of solutions includes both directly differential resistance-to-digital converter, and differential resistance-to-time converter. One advantage of this solution compared with the first example technique is an increase of the sensitivity and SNR. However, the matching of the two resistors would still be a concern.

In a third example technique for measuring electrical resistance, an additional cancellation circuit is used to memorize the baseline resistance in analogue memory. This technique does not have the resistor matching problem of the first two, but requires an analogue memory to provide the baseline resistance value acquired from an additional calibration phase. In addition, the matching of the transistors in the baseline cancellation circuit also influences the accuracy of final results.

Instead of the three techniques mentioned above, a ratiometric resistance-to-digital converter (RDC) measures a thermal resistance of gas-sensitive device relative to that of a reference device, which is insensitive or less sensitive to the target gas. Using such a ratiometric RDC, an absolute baseline thermal resistance accuracy requirement can be shifted to a matching requirement of the sensitive and reference devices, and the power stability requirements would be relaxed.

In one example embodiment the ratiometric measurement is performed using resistors made by a same material and used as both sensor and reference devices. In addition, the ratiometric nature of the RDC is capable of narrowing the full scale of the RDC, thereby reducing the required dynamic range of resistance measurements. The technique is therefore well suited to interfacing the resistive sensors devoted to thermal conductivity measurement, in which small changes in resistance need to be digitized in the presence of a relatively large baseline resistance.

According to another example embodiment, a ratiometric device, comprising: a current source having a first current, a second current different from the first current, and a current-select program; a sensor device responsive to a gas and having a sensor-cold temperature T(cold,sens) in response to the first current and a sensor-hot temperature T(hot,sens) in response to the second current; a reference device having a reference-cold temperature T(cold,ref) in response to the first current and a reference-hot temperature T(hot,ref) in response to the second current; and wherein the ratiometric device includes a temperature difference ratio output based on T(cold,sens), T(hot,sens), T(cold,ref) and T(hot,ref).

According to yet another example embodiment, an article of manufacture comprises at least one non-transitory, tangible machine readable storage medium containing executable machine instructions for ratiometric measurement which comprise: generating a first current and a second current different from the first current; switching between the first and second currents at a current-select program; measuring, from a sensor device responsive to a gas, a sensor-cold temperature T(cold,sens) in response to the first current and a sensor-hot temperature T(hot,sens) in response to the second current; measuring, from a reference device a reference-cold temperature T(cold,ref) in response to the first current and a reference-hot temperature T(hot,ref) in response to the second current; wherein the reference device is less responsive to the gas than the sensor device; and calculating a temperature difference ratio; and generating a thermal conductivity device output signal based on the temperature difference ratio.

The above discussion/summary is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

Figure 1A:
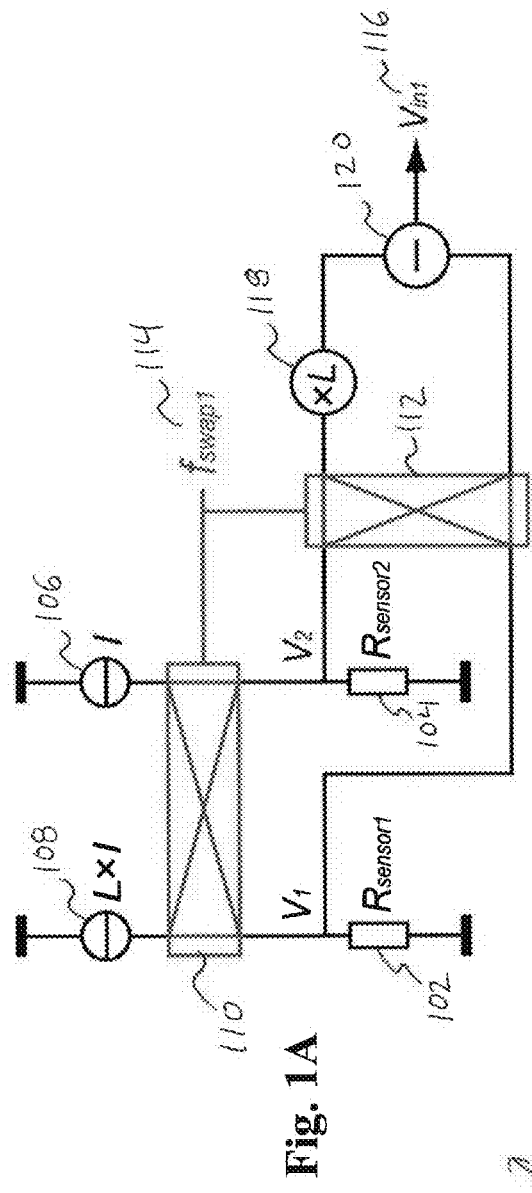
FIGS. 1A and 1B are an example of a first ratiometric device.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

An example thermal conductivity/resistivity measurement device is now discussed. In one example, the device employs a ratiometric measurement technique which lessens the challenge of implementing an accurate power reference. In another example, the device employs baseline resistance cancellation techniques which reduce the dynamic range of the electrical resistance measurement needed for thermal conductivity/resistivity measurements without the concerns mentioned above. In yet another example, the device employs a temperature compensation structure which reduces or omits the temperature dependency of the thermal conductivity/resistivity measurement device. Each of these three techniques are now discussed in turn.

Ratiometric Measurement Technique

Based on the principle of thermal conductivity measurement, in order to accurately measure presence and concentration of a gas, for example carbon-dioxide $CO_2$, the dissipated power needs to be very stable. Sensitivity analysis shows that the stability requirement on the power reference is normally quite high (e.g. for 100 ppm accuracy of $CO_2$ concentration, the variation of the power reference in one example embodiment needs to be within ±50 ppm).

Therefore, instead of measuring absolute thermal resistance of a sensor device (aka. gas sensor, transducer, hot wire sensor, or sensing resistor, or $CO_2$-sensitive device), measuring a thermal resistance of the sensor device relative to that of a reference device which is less sensitive to (or in another embodiment, shielded from) a gas to be sensed (e.g. $CO_2$) relaxes the power reference stability requirement. Using this technique, the absolute power reference accuracy requirement can now be shifted to a matching requirement of the sensor device and reference device. In various embodiments, the reference device can be at least one of: a device which has similar thermal properties as the sensor device; a thermal conductivity reference device; or a device which is the similar to the sensor device but having a different thermal sensitivity.

Figure 1B:
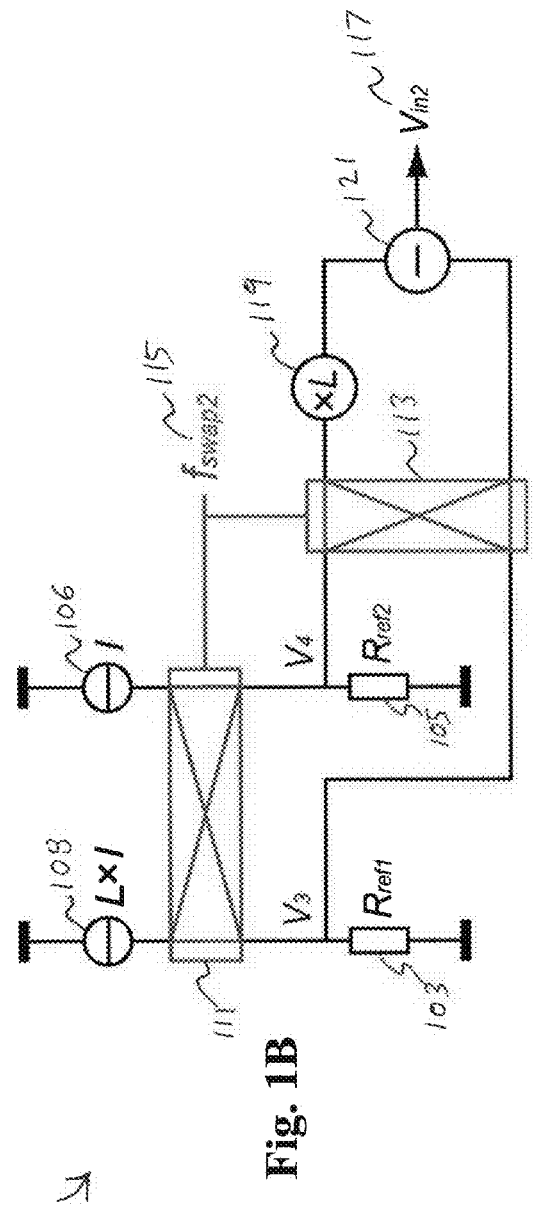

FIGS. 1A and 1B are an example of a first ratiometric device 100 (e.g. front-end sensor). The first ratiometric device 100 includes two sensor devices 102, 104 which are exposed to a gas to be sensed, and two reference devices 103, 105 which are not exposed to the gas to be sensed.

Figure 2:
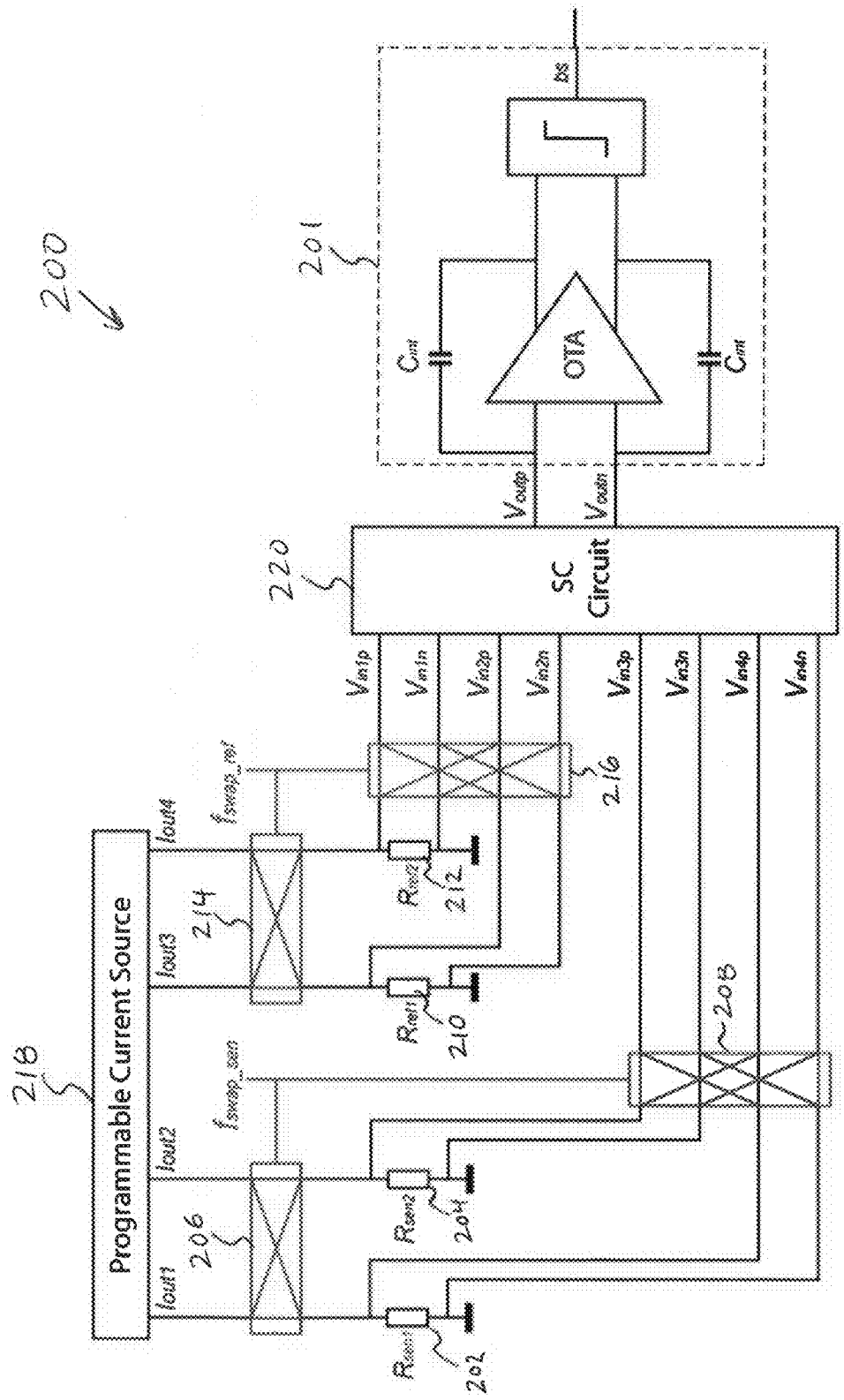
FIG. 2 is an example of a second ratiometric device.

In one example, the two reference devices 103, 105 use a same circuit wiring configuration and/or physical dimensions as the two sensor devices 102, 104. Another example embodiment of sensor and reference devices are also shown in FIG. 2, discussed below. As suggested by the "R" labels, in one example embodiment the sensor and reference devices 103, 105 are resistors.

The reference devices 103, 105 in one example are included in a same package as the sensor devices 102, 104. In another example, the reference devices 103, 105 are included in a different package than the sensor devices 102, 104. This different package can be either on a separately sealed die in a same package as the sensor devices 102, 104, or in a separate package which is also hermetically sealed so that the reference sensor is not exposed to a gas to be sensed. The reference devices can also differ from the sensor devices by their geometry.

The two sensor devices 102, 104, as well as the two reference devices 103, 105, are biased at two different current levels first current (I) 106 and second current (L×I) 108 (aka. "L·I" where "×" or "·" are both multiplication symbols and L is a number) so that four different temperatures are generated: $T_{hot,sens}$, $T_{cold,sens}$, $T_{hot,ref}$ and $T_{cold,ref}$. Herein defined, "hot" refers to a device carrying a greater current (L×I) and "cold" refers to a device carrying a lesser current (I). The actual temperatures of the devices may vary during operation and between different example embodiments.

While the example embodiment in FIG. 1 shows two constant current sources 106 and 108 which are used for determining the temperature of a pair of devices (e.g. the sensor devices 102, 104 or the reference devices 103, 105) under varying current loads (e.g. hot and cold current levels), in an alternate embodiment only one sensor device and one reference device can be operated in a time-multiplexed manner to collect a same set of temperature measurement data. In such an embodiment, a programmable (or switchable) current source (not shown in FIG. 1) supplies the two different current levels 106, 108 according to a current-select program. The current-select program switches/swaps the current levels 106, 108 at either a periodic or non-periodic rate which can be fixed or variable.

Two lower temperatures $T_{cold,sens}$ and $T_{cold,ref}$ serve as 'local' ambient temperatures for the sensor devices 102, 104 and reference devices 103, 105 respectively, and the parameter to be measured is:

$$\frac{\Delta T_{sens}}{\Delta T_{ref}} = \frac{T_{hot,sens} - T_{cold,sens}}{T_{hot,ref} - T_{cold,ref}} \quad (2)$$

By measuring a ratio of temperature difference (i.e. ratiometric measurement) according to equation 2, ambient temperature variations appear as a common mode impact for the 'hot' and 'cold' devices.

As shown in equation 3, the thermal resistance ratio can be expressed by the ratio of the temperature difference multiplied by the ratio of the power difference:

$$\frac{\theta_{sens}}{\theta_{ref}} = \left(\frac{\Delta T_{sens}}{\Delta T_{ref}}\right) \cdot \left(\frac{\Delta P_{ref}}{\Delta P_{sens}}\right) = \quad (3)$$

$$\left(\frac{R_{hot,sens} - R_{cold,sens}}{R_{hot,ref} - R_{cold,ref}}\right) \cdot \left(\frac{R_{0,ref} \cdot \alpha_{ref}}{R_{0,sens} \cdot \alpha_{sens}}\right) \cdot \left(\frac{L^2 \cdot R_{hot,ref} - R_{cold,ref}}{L^2 \cdot R_{hot,sens} - R_{cold,sens}}\right)$$

in which $R_0$ is the nominal resistance at a reference temperature (e.g. 20° C.) and α is the temperature dependence of the resistor.

If the nominal resistances and temperature dependence of sensor devices 102, 104 and reference devices 103, 105 are stable, the second term of the equation is a constant value and only the first and last terms need to be measured. If the bias first current I 106 and second current L·I 108 are substituted in, equation (3) is changed to:

$$\frac{\theta_{sens}}{\theta_{ref}} = \quad (4)$$

$$\left(\frac{V_{hot,sens} - L \cdot V_{cold,sens}}{V_{hot,ref} - L \cdot V_{cold,ref}}\right) \cdot \left(\frac{L \cdot V_{hot,ref} - V_{cold,ref}}{L \cdot V_{hot,sens} - V_{cold,sens}}\right) \cdot \text{CONSTANT}$$

Therefore, a gas dependent thermal resistance ratio can be obtained with the assistance of a readout circuit (not shown in FIG. 1) to resolve the two voltage ratios.

Baseline Resistance Cancellation Technique:

With the addition of device swap switches 110, 111, 112, 113 operated at f(swap) frequencies 114, 115 as shown in FIG. 1, the two sensor devices 102, 104 biased at two different current levels (I 106 and L·I 108) can be swapped dynamically during device 100 operation. In one example embodiment, the device swap switches 110, 111, 112, 113 use chopper circuits to perform the switching operation; however other switching devices can be used.

The two-level currents (I 106 and L·I 108) provide hot-and-cold measurements for both of the two sensor devices 102, 104 and two reference devices 103, 105 so as to acquire heated resistance and baseline resistance at the f(swap) frequencies 114, 115. The practical mismatch of the baseline resistances is cancelled out by the dynamic swapping during device 100 operation.

As illustrated in FIG. 1, when the device swap switches 110, 111, 112, 113 are in straight connection (which was the case during the ratiometric measurement technique discussed above), $R_{sensor1}$ 102 is biased at a higher level current L×I 108, while $R_{sensor2}$ 104 is biased at a lower level current I 106. Therefore $V_{in}$ 116 (and correspondingly $V_{in}$ 117 for the reference devices 103, 105) is directly proportional to the difference of the heated resistance of $R_{sensor1}$ 102 ($R_{sensor1,hot}$) and the cold resistance ($R_{sensor2,cold}$). The cold (i.e. low current I 106) voltage (V2) is multiplied by voltage multiplier (×L) 118, 119 and the baseline resistance of $R_{sensor2}$ 104 ($R_{sensor2,cold}$) as shown in equation 5:

$$V_{in} = L \cdot I \cdot (R_{sensor1,hot} - R_{sensor2,cold}) \quad (5)$$

Similarly, when the device swap switches 110, 111, 112, 113 are in cross connection, $R_{sensor1}$ 102 is biased at a lower level (i.e. cold) current I 106, while $R_{sensor2}$ 104 is biased at a higher level (i.e. hot) current L×I 106. Therefore $V_{in}$ 116 (and correspondingly $V_{in}$ 117 for the reference devices 103, 105) represents the difference of the heated resistance of $R_{sensor2}$ 104 ($R_{sensor2,hot}$) and the baseline resistance of $R_{sensor1}$ 102 ($R_{sensor1,cold}$) as shown in equation 6:

$$V_{in} = L \cdot I \cdot (R_{sensor2,hot} - R_{sensor1,cold}) \quad (6)$$

During device 100 operation, the device swap switches 110, 111, 112, 113 are switched between straight and cross connections at the f(swap) frequencies 114, 115. Thus an effective resistance difference $\Delta R_{eff}$ is equal to the average of $R_{sensor1,hot}$ and $R_{sensor2,hot}$ subtracted by the average of $R_{sensor1,cold}$ and $R_{sensor2,cold}$ as shown in equation 7:

$$\Delta R_{eff}\left(\frac{R_{sensor1,hot} + R_{sensor2,hot}}{2}\right) - \left(\frac{R_{sensor1,cold} + R_{sensor2,cold}}{2}\right) \quad (7)$$

Using the device swap switches 110, 111, 112, 113 and f(swap) frequencies 114, 115 as described above, any mismatch of the baseline resistances of the two sensor resistors does not impact the ratiometric measurement, since the measured resistance change is a difference of the averaged hot resistances and the averaged cold resistances of the two sensor resistors. In one example embodiment, any initial mismatch is minimized by trimming (see FIG. 3) so as not to overload subsequent analog to digital voltage conversions (ADC) (e.g. of V(in) 116, 117).

Figure 4:
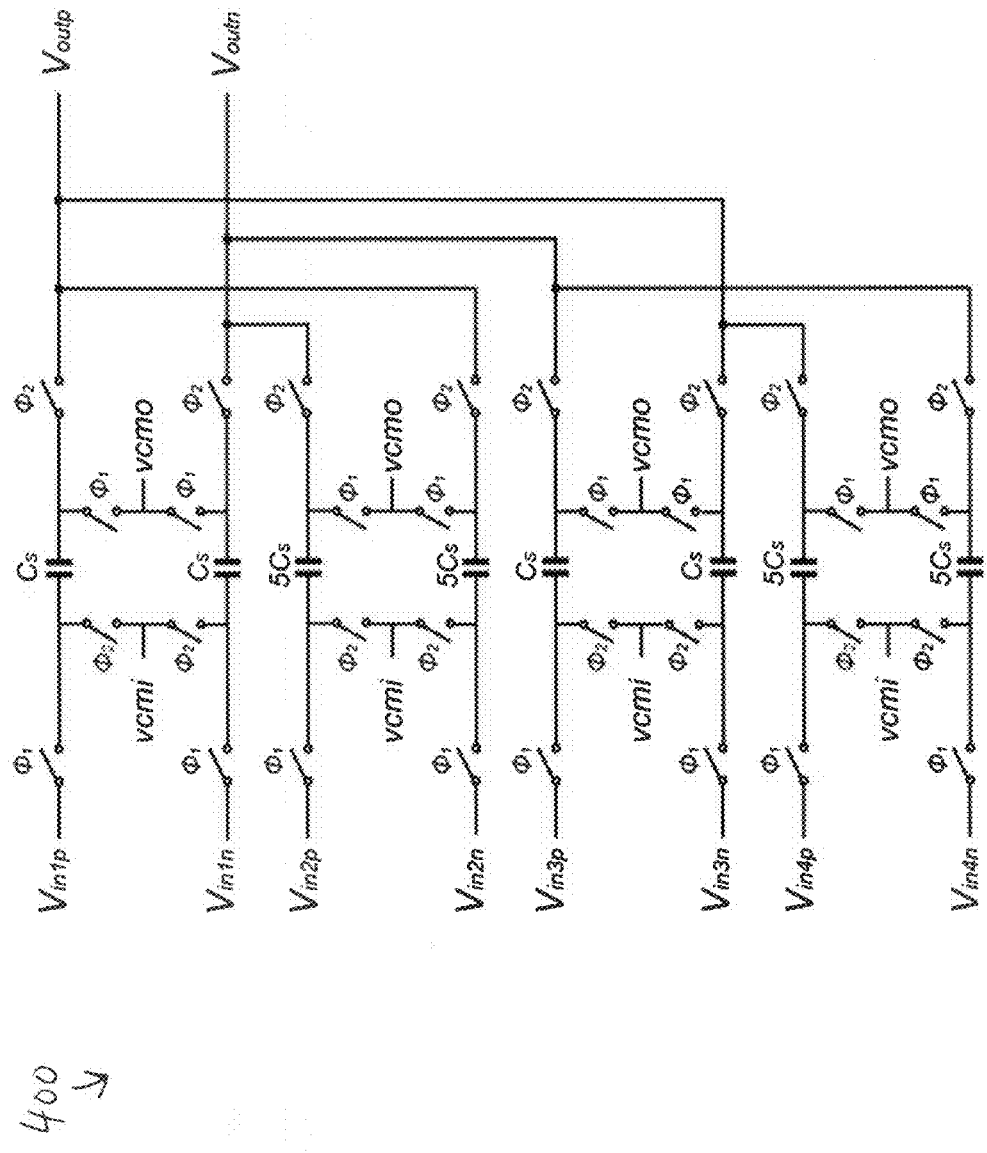
FIG. 4 is an example a first switched-capacitor circuit within the second ratiometric device.
Figure 5:
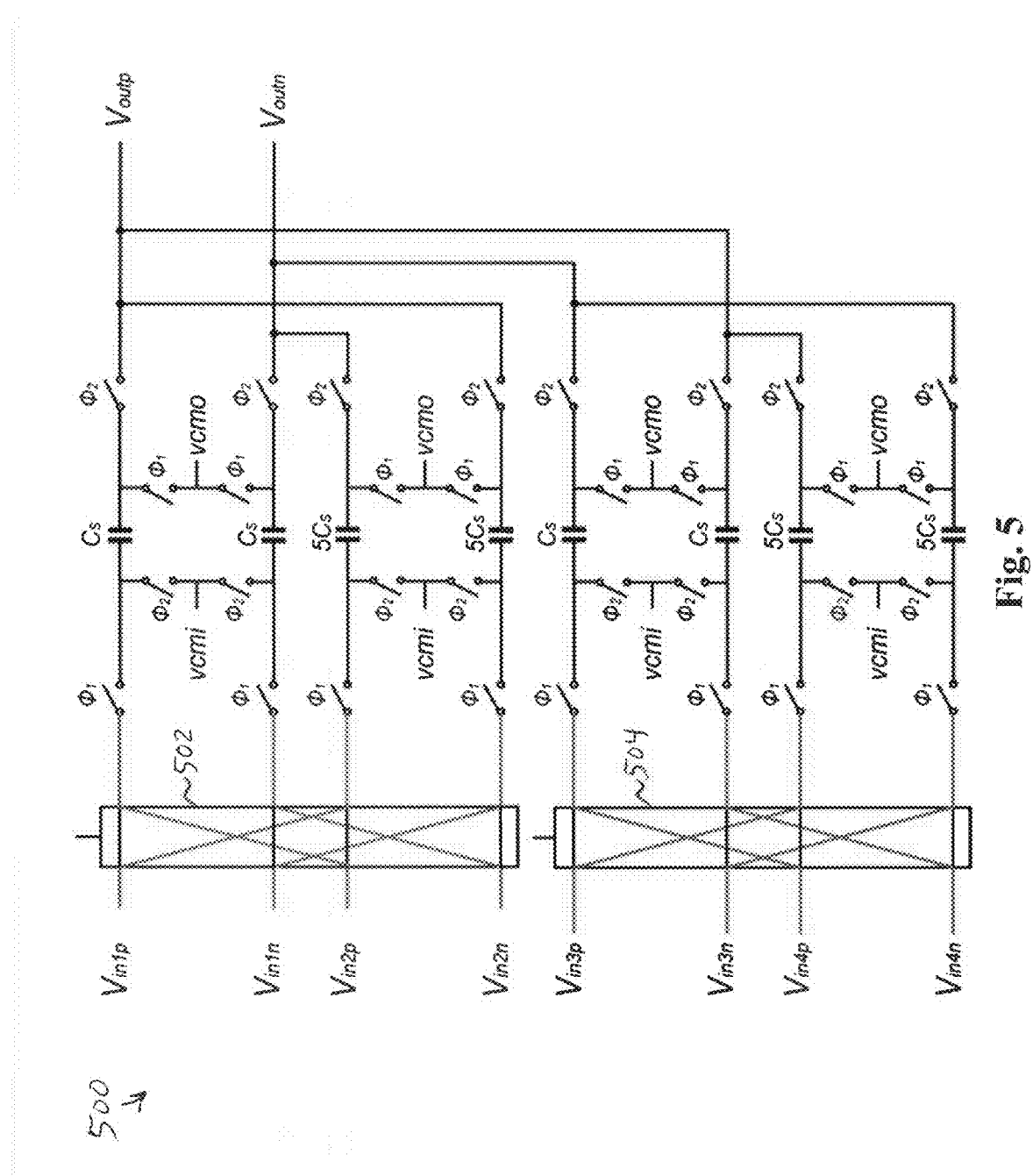
FIG. 5 is an example a second switched-capacitor circuit within the second ratiometric device.

In one example embodiment, the voltage multiplier (×L) 118, 119 and subtraction block 120, 121 can be implemented using a switched-capacitor circuit such as shown in FIG. 4 and FIG. 5.

FIG. 2 is an example of a second ratiometric device 200 (e.g. front-end sensor) using a ΣΔ modulator ADC 201. The second ratiometric device 200 measures the ratio of thermal conductance in thermal conductivity based gas sensor applications. As discuss with respect to equation 1, one example of measuring thermal conductance uses both temperature and power information. To achieve this, the second ratiometric device 200 can be configured into either a temperature measurement mode, a power measurement mode or variable temperature and power measurement modes. A ratio of thermal conductivities can then be obtained by combining the results obtained in these two modes.

In FIG. 2, two sensor resistors 202, 204 biased at two different current levels I(out1) and I(out2) are dynamically swapped using device swap switches 206, 208 to cancel or reduce out any mismatch between them. In addition, two reference resistors 210, 212 are also employed and operated in a similar manner as discussed earlier with respect to ratiometric measurement in FIG. 1. The two reference resistors 210, 212, are biased at current levels I(out3) and I(out4) are dynamically swapped using device swap switches 214, 216 to cancel out any mismatch between them. The currents I(out1), I(out2), I(out3) and I(out4) are generated by a programmable current source 218, such as shown in FIG. 3 and now discussed.

Figure 3:
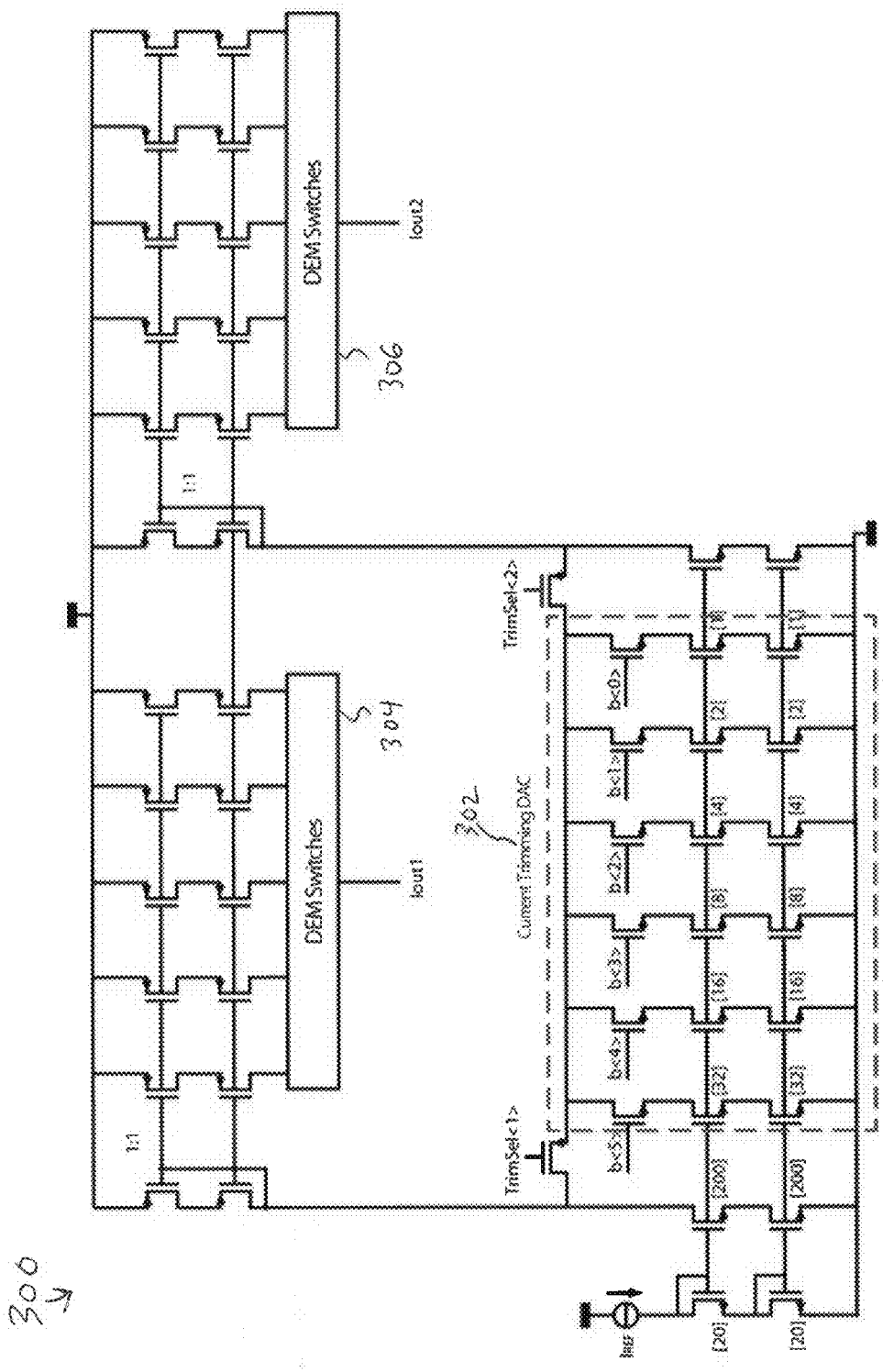
FIG. 3 is an example programmable current source within the second ratiometric device.

FIG. 3 is an example 300 programmable current source 218 with a current trimming function 302 within the second ratiometric device 200. Only two current outputs I(out1), I(out2) are shown in FIG. 3, instead of all four, however I(out3) and I(out4) are generated in a similar way.

The output currents of the programmable current source 218 are digitally controlled such that when one sensor resistor 202 or 204 is being biased at a lower current level, the other sensor resistor 204 or 202 is being biased at a higher current level (vice versa). The same digitally control technique is also controls the reference resistors' 210, 212 currents I(out3) and I(out4).

In the example shown in FIG. 3, each pair of the output currents are switched between a unit current (lower/cold level) and five times (or some other multiple of) the unit current (higher/hot level), and dynamic element matching (DEM) logic 304, 306 is adopted so as to generate an accurate current ratio (e.g. L=5).

Although the mismatch of the sensor (reference) resistors will not influence the accuracy of the measured $\Delta R_{eff}$ (as discussed with respect to equation 4), the current trimming function 302 can be included to reduce the mismatch to a level that will not overload a ΣΔ modulator. A current ratio between $I_{out1}$ and $I_{out2}$ (and also between $I_{out3}$ and $I_{out3}$) does not need to be maintained, as the effective sensor resistor is an average of the two sensor resistors and the DEM 304, 306 provides an accurate current ratio for the hot-and-cold measurements of the effective sensor resistor by sequentially generating an accurate current ratio of five for each current output.

Returning to FIG. 2, voltages across the hot and cold resistors, V(in1p), V(in1n), V(in2p), V(in2n), V(in3p), V(in3n), V(in4p), V(in4n), are sampled with a switched-capacitor circuit 220 (SC Circuit), examples of which are shown in FIG. 4 and FIG. 5.

FIG. 4 is an example a first switched-capacitor circuit 400 within the second ratiometric device 200 whereby the second ratiometric device 200 is configured for the temperature measurement mode. In the circuit of FIG. 4, capacitors having values $C_s$ and $5C_s$ are used to sample the voltages across the hot and cold resistors.

Returning to FIG. 2, the signal that will be digitized by the $\Sigma\Delta$ modulator ADC 201 is a ratio of the change in the effective reference resistor and that in the effective sensor resistor:

$$\mu_1 = \frac{V_{hot,ref(eff)} \cdot C_S - V_{cold,ref(eff)} \cdot 5C_S}{V_{hot,sen(eff)} \cdot C_S - V_{cold,sen(eff)} \cdot 5C_S} = \frac{R_{hot,ref(eff)} - R_{cold,ref(eff)}}{R_{hot,sen(eff)} - R_{cold,sen(eff)}} = \quad (8)$$

$$\frac{\Delta R_{eff,reference}}{\Delta R_{eff,sensor}} = \frac{\Delta T_{eff,reference} \cdot TCR_{reference}}{\Delta T_{eff,sensor} \cdot TCR_{sensor}}$$

In equation 8, $\mu_1$ is a bit stream density of this charge-balancing $\Sigma\Delta$ modulator ADC 201. If the sensor resistors 202, 204 and reference resistors 210, 212 are made by the same material, they should have the same temperature coefficient (TCR). Therefore a temperature difference ratio can be attained from equation 8.

If the example time-multiplexed embodiment (introduced above) is used, instead of having the pair of devices (i.e. either the pair of sensor resistors 202, 204 and/or the pair of reference resistors 210, 212) to obtain the hot and cold resistances simultaneously, only one sensor resistor 202 and reference resistor 210 are needed and which are operated in a time-multiplexed manner. In this scenario, the programmable current source 218 is digitally controlled to generate the unit current I(out1) and the multiplied current I(out2) serially (e.g. alternately). When the baseline resistance needs to be measured, the sensor resistor is biased at the unit current and the voltage across it will be sampled on the multiplied capacitor (5Cs). Then when the hot resistance needs to be measured, the sensor resistor is biased at the higher current (5*I) and the generated voltage is sampled on the unit capacitor (Cs). The same operations are applied to the one reference resistor. Thus the result indicated by equation 8 can be obtained similarly.

In one example embodiment, any mismatch of Cs and 5Cs can be solved by Dynamic Elements Matching (DEM), wherein 5 unit capacitors (each of them has a typical value of Cs) are dynamically connected to the voltage inputs to be sampled in a time-interleaved manner. In this case, one sigma-delta period contains 2 sampling cycles. In the first sampling cycle, only the first unit capacitor is connected to the first input (e.g., Vhot) to sample the voltage and transfer charge to the integrator. In next sampling cycle, all 5 unit capacitors are connected to the second input (e.g., Vcold) to sample the voltage and transfer charge to the integrator. Similarly, in the following sigma-delta periods, only the second, third, fourth, or fifth unit capacitor is connected to the first input. The output of the RDC effectively reflects the average of the capacitor ratios among all cycles, and therefore an accurate 1:5 ratio of the capacitors is attained.

In a second example embodiment of the capacitor DEM, in one RDC conversion cycle, the voltages cold and hot voltages are sampled with unit capacitors. The first voltage (eg. Vhot) is sampled by 5 capacitors, the second voltage is sampled by 1 unit capacitor Cs. Then in the next cycles, the unit capacitor are switched to the first voltage sequentially, the remaining capacitors sampling the second voltage one by one. In this way a very accurate 1:5 ratio is obtained at the cost of a six times higher clock frequency.

In a third example embodiment, only one unit capacitor is used to sample the first and second voltage. For example,
first the first voltage is sampled, in a next phase the second voltage is sampled 5 times, also leading to a very accurate 1:5 ratio.

In other example embodiments, a combination of the above DEM techniques or alternative DEM techniques can be implemented to achieve accurate capacitor ratios.

FIG. 5 is an example a second switched-capacitor circuit within the second ratiometric device whereby the second ratiometric device 200 is configurable between the temperature and the power measurement modes by the addition of switches 502, 504 at the inputs of the switched-capacitor circuit 220. The switches 502, 504 multiplex the input voltages so that the voltages across the hot and cold resistors are now sampled at $5C_s$ and $C_s$ respectively. Thus, the signal to be digitized in power measurement mode is a ratio of power difference between hot and cold measurement of the effective reference resistor (average of the two reference resistors) and that of the effective sensor resistor (average of the two sensor resistors) as shown in equation 9:

$$\mu_2 = \frac{\Delta P_{eff,reference}}{\Delta P_{eff,sensor}} = \quad (9)$$

$$\frac{(5I)^2 \cdot R_{hot,ref(eff)} - I^2 \cdot R_{cold,ref(eff)}}{(5I)^2 \cdot R_{hot,sen(eff)} - I^2 \cdot R_{cold,sen(eff)}} = \frac{5 \cdot V_{hot,ref(eff)} - V_{cold,ref(eff)}}{5 \cdot V_{hot,sen(eff)} - V_{cold,sen(eff)}}$$

A thermal conductance ratio of the sensor resistors 202, 204 and reference resistors 210, 212 can then be derived by combining the measured temperature difference ratio and the power difference ratio in accordance with equation 10:

$$\frac{\theta_{eff,reference}}{\theta_{eff,sensor}} = \frac{\Delta T_{eff,reference}}{\Delta T_{eff,sensor}} \cdot \frac{\Delta P_{eff,sensor}}{\Delta P_{eff,reference}} = \frac{\mu_1}{\mu_2} \quad (10)$$

Temperature Compensation Structure

Figure 6:
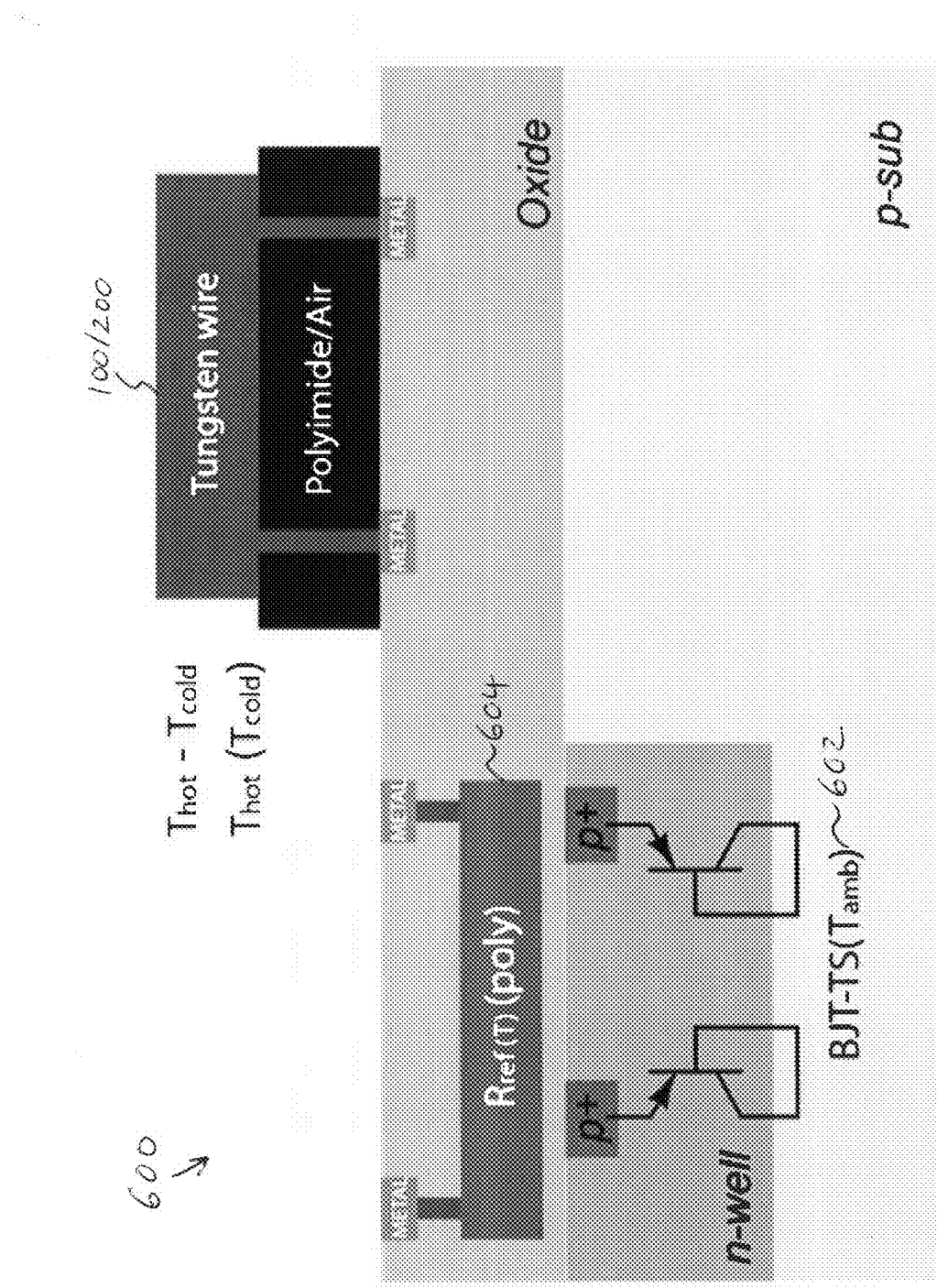
FIG. 6 is an example of a vertical cross-section of temperature compensation device within either the first or second ratiometric devices.

FIG. 6 is an example of a vertical cross-section of temperature compensation structure 600 which can be incorporated into either the first or second ratiometric devices 100, 200. The temperature compensation structure 600 cancels out residual temperature dependency of a thermal conductivity sensor. In one example, such residue temperature dependency cancelation requires both the temperature of the sensor and reference devices and the ambient temperature.

To accomplish this, the temperature compensation structure 600 includes an auxiliary BJT temperature sensor 602 and a poly resistor 604 with low temperature coefficient. The sensor devices 102, 104 and reference devices 103, 105, from FIG. 1, or sensor resistors 202, 204 and reference resistors 210, 212, from FIG. 2, are measured relative to the on-chip poly resistor 604 whose temperature dependency is compensated by a the substrate-BJT temperature sensor 602 placed in close proximity to the poly resistor 604. The BJT temperature sensor 602 is also able to measure a temperature of the substrate which is considered as the local ambient of the thermal conductivity sensor.

Figure 7:
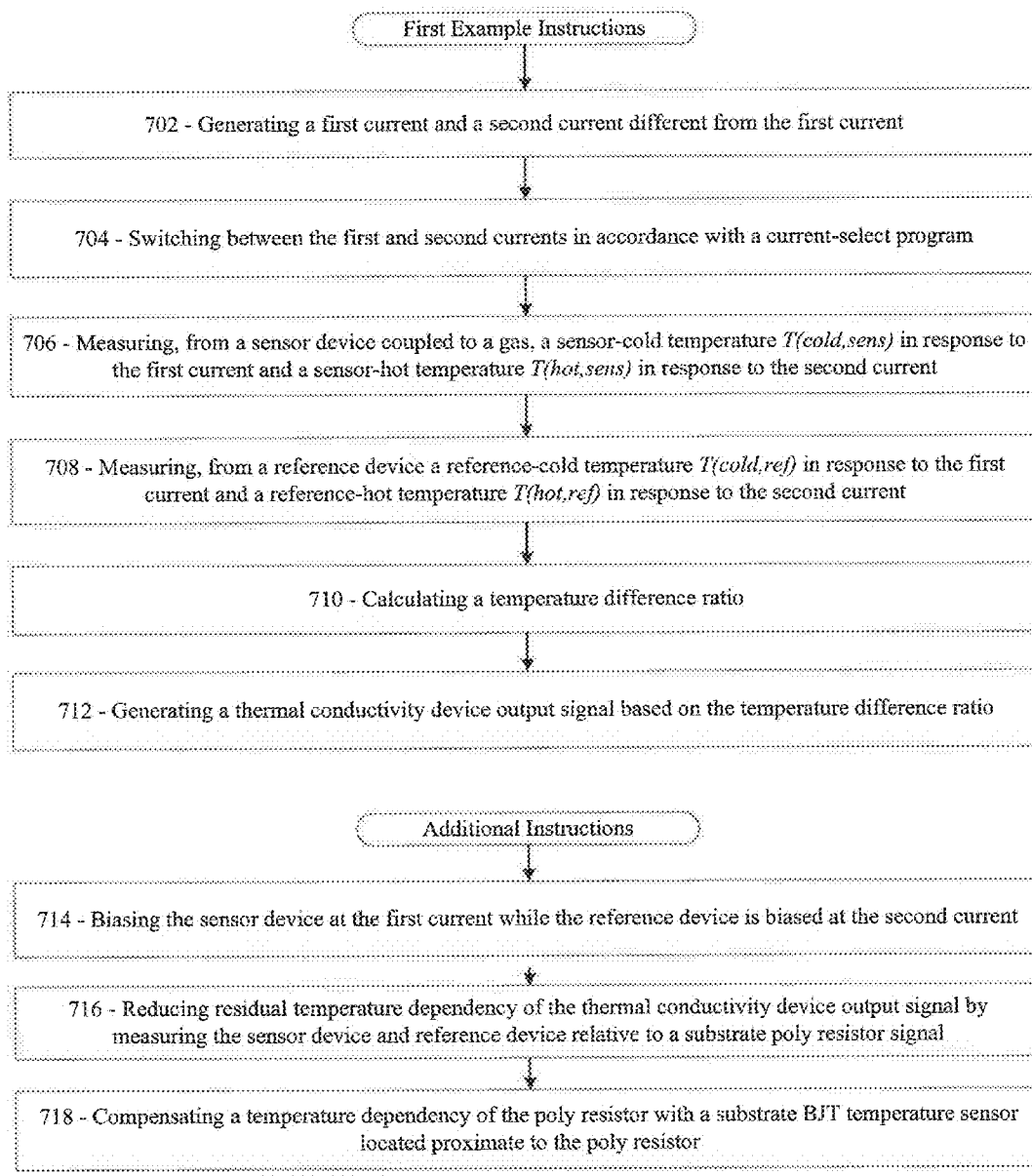
FIG. 7 is an example set of ratiometric instructions.

FIG. 7 is an example list of instructions for enabling a ratiometric device. The order in which the instructions of FIG. 7 are discussed does not limit the order in which other example embodiments implement the instructions. Additionally, in some embodiments the instructions are implemented concurrently. A first example instructions set begins in 702, by generating a first current and a second current different from the first current. Next, in 704, switching between the first and second currents in accordance with a current-select program. Then in 706, measuring, from a sensor device coupled to a gas, a sensor-cold temperature T(cold,sens) in response to the first current and a sensor-hot temperature T(hot,sens) in response to the second current. In 708, measuring, from a reference device shielded from the gas or less sensitive to it, a reference-cold temperature T(cold,ref) in response to the first current and a reference-hot temperature T(hot,ref) in response to the second current. Then in 710, calculating a temperature difference ratio based on this equation:

$$\frac{\Delta T_{sens}}{\Delta T_{ref}} = \frac{T_{hot,sens} - T_{cold,sens}}{T_{hot,ref} - T_{cold,ref}}$$

And then in 712, generating a thermal conductivity device output signal based on the temperature difference ratio.

The instructions can be augmented with one or more of the following additional instructions, presented in no particular order. In 714, biasing the sensor device at the first current while the reference device is biased at the second current. In 716, reducing residual temperature dependency of the thermal conductivity device output signal by measuring the sensor device and reference device relative to a substrate poly resistor signal. In 718, compensating a temperature dependency of the poly resistor with a substrate BJT temperature sensor located proximate to the poly resistor.

Figure 8:
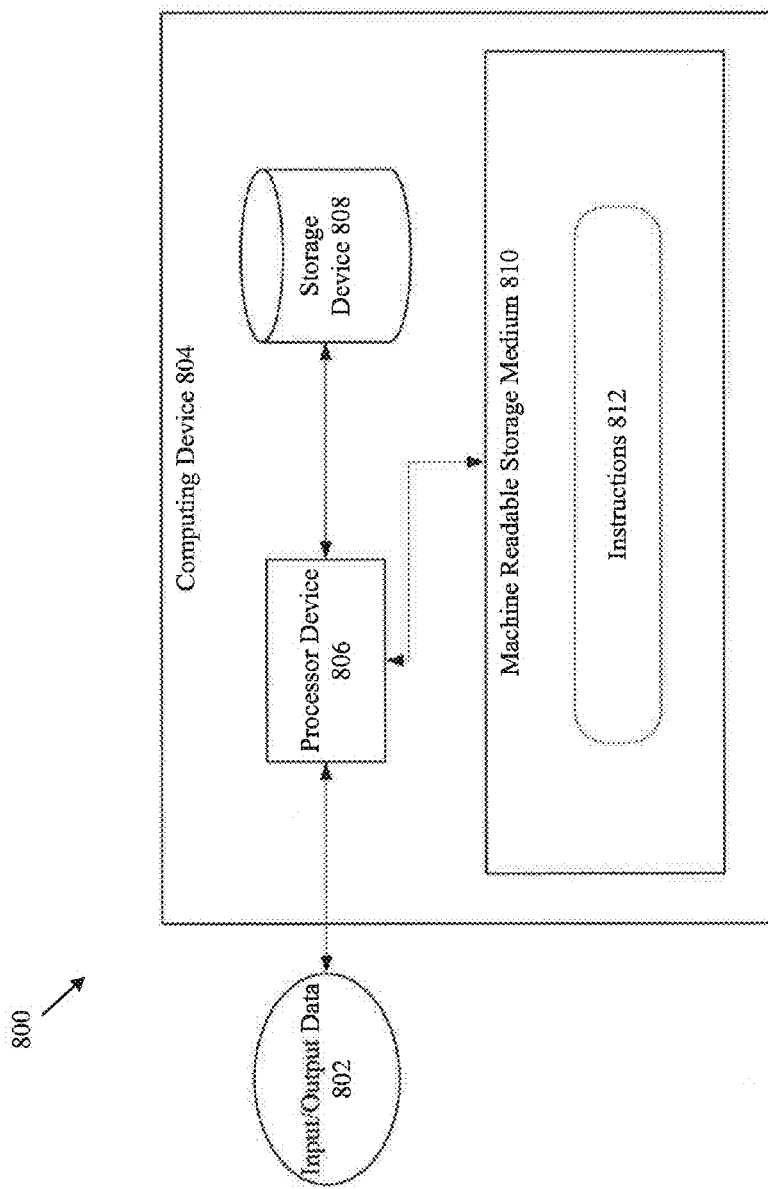
FIG. 8 is an example of a third ratiometric device.

FIG. 8 is an example of a third ratiometric device 800. The system 800 shows an input/output data 802 interface with an electronic apparatus 804. The electronic apparatus 804 includes a processor 806, a storage device 808, and a machine-readable storage medium 810. The machine-readable storage medium 810 includes instructions 812 which control how the processor 806 receives input data 802 and transforms the input data into output data 802, using data within the storage device 808. Example instructions 812 stored in the machine-readable storage medium 810 are discussed elsewhere in this specification. The machine-readable storage medium in an alternate example embodiment is a computer-readable storage medium.

The processor (such as a central processing unit, CPU, microprocessor, application-specific integrated circuit (ASIC), etc.) controls the overall operation of the storage device (such as random access memory (RAM) for temporary data storage, read only memory (ROM) for permanent data storage, firmware, flash memory, external and internal hard-disk drives, and the like). The processor device communicates with the storage device and non-transient machine-readable storage medium using a bus and performs operations and tasks that implement one or more blocks stored in the machine-readable storage medium. The machine-readable storage medium in an alternate example embodiment is a computer-readable storage medium.

The blocks which comprise the instructions and/or flowcharts in the above Figures can be executed in any order, unless a specific order is explicitly stated. Also, those skilled in the art will recognize that while one example set of instructions have been discussed, the material in this specification can be combined in a variety of ways to yield other examples as well, and are to be understood within a context provided by this detailed description.

In some example embodiments the set of instructions described above are implemented as functional and software instructions embodied as a set of executable instructions which are effected on a computer or machine which is programmed with and controlled by said executable instructions. Such instructions are loaded for execution on a processor (such as one or more CPUs). The term processor includes microprocessors, microcontrollers, processor modules or subsystems (including one or more microprocessors or microcontrollers), or other control or computing devices. A processor can refer to a single component or to plural components.

In one example, one or more blocks or steps discussed herein are automated. The terms automated or automatically (and like variations thereof) mean controlled operation of an apparatus, system, and/or process using computers and/or mechanical/electrical devices without the necessity of human intervention, observation, effort and/or decision.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A ratiometric device for sensing a gas concentration, comprising:
    a programmable or switchable current source providing a first current and a second current different in value from the first current, wherein the programming or switching of the current source is selected by a current select program;
    at least one sensor device which is exposed to and responsive to a gas to be sensed, which has a first sensor temperature, denoted by T(cold,sens), when the first current is selected, and has a second sensor temperature, denoted by T(hot,sens), when the second current is selected;
    at least one reference device which is not exposed to the gas to be sensed, which has a first reference temperature, denoted by T(cold,ref), when the first current is selected, and has a second reference temperature, denoted by T(hot,ref), when the second current is selected; and
    a readout circuit arranged to measure a first and second sensor voltage indicative of the first and second sensor temperature, respectively, and arranged to measure a first and second sensor voltage indicative of the first and second reference temperature, respectively, and further arranged to obtain from the measured voltages a temperature difference ratio $T_{sens}/T_{ref}$ expressed by:

$$\frac{T_{sens}}{T_{ref}} = \frac{T_{hot,sens} - T_{cold,sens}}{T_{hot,ref} - T_{cold,ref}},$$

wherein an output signal of the ratiometric device is generated depending on the temperature difference ratio $T_{sens}/T_{ref}$; and
    wherein the output signal is indicative of a thermal resistance ratio $\theta_{sens}/\theta_{ref}$ depending on a gas concentration of the gas to be sensed.

2. The device of claim 1, wherein the sensor device is a first sensor resistor having a resistance R(sensor1,cold) and a resistance R(sensor1,hot),
    the device further comprising a second sensor resistor coupled to the gas and having a sensor-cold resistance R(sensor2,cold) in response to the first current and a sensor-hot resistance R(sensor2,hot) in response to the second current, wherein the ratiometric device includes effective sensor resistance difference $\Delta R_{\mathit{eff}}$ output based on this equation:

$$\Delta R_{\mathit{eff}} = \left(\frac{R_{sensor1,hot} + R_{sensor2,hot}}{2}\right) - \left(\frac{R_{sensor1,cold} + R_{sensor2cold}}{2}\right).$$

3. A ratiometric device comprising:

a current source having a first current, a second current different from the first current, and a current-select program;

a sensor device responsive to a gas and having a sensor-cold temperature T(cold,sens) in response to the first current and a sensor-hot temperature T(hot,sens) in response to the second current; and a reference device having a reference-cold temperature T(cold,ref) in response to the first current and a reference-hot temperature T(hot,ref) in response to the second current, wherein the ratiometric device includes a temperature difference ratio output based on this equation:

$$\frac{\Delta T_{sens}}{\Delta T_{ref}} = \frac{T_{hot,sens} - T_{cold,sens}}{T_{hot,ref} - T_{cold,ref}},$$

wherein the sensor device is a first sensor resistor having a resistance R(sensor1,cold) and a resistance R(sensor1,hot);

a second sensor resistor coupled to the gas and having a sensor-cold resistance R(sensor2,cold) in response to the first current and a sensor-hot resistance R(sensor2,hot) in response to the second current, wherein the ratiometric device includes effective sensor resistance difference $\Delta R_{\mathit{eff}}$ output based on this equation:

$$\Delta R_{\mathit{eff}} = \left(\frac{R_{sensor1,hot} + R_{sensor2,hot}}{2}\right) - \left(\frac{R_{sensor1,cold} + R_{sensor2,cold}}{2}\right),$$

wherein the reference device is a first reference resistor having a resistance R(ref1,cold) and a resistance R(ref1,hot); and a second reference resistor having a reference-cold resistance R(ref2,cold) in response to the first current and a reference-hot resistance R(ref2,hot) in response to the second current, wherein the second reference device is less responsive to the gas than the sensor device and second sensor resistor, and wherein the ratiometric device includes effective reference resistance difference $\Delta R_{\mathit{eff}}$ output based on this equation:

$$\Delta R_{\mathit{eff}} = \left(\frac{R_{ref\cdot 1,hot} + R_{ref\cdot 2,hot}}{2}\right) - \left(\frac{R_{ref\cdot 1,cold} + R_{ref\cdot 2,cold}}{2}\right).$$

4. The device of claim 1, further comprising a switched-capacitor circuit having an output derived from voltages across the sensor device and the reference device.

5. A ratiometric device comprising:

a current source having a first current, a second current different from the first current, and a current-select program;

a sensor device responsive to a gas and having a sensor-cold temperature T(cold,sens) in response to the first current and a sensor-hot temperature T(hot,sens) in response to the second current;

a reference device having a reference-cold temperature T(cold,ref) in response to the first current and a reference-hot temperature T(hot,ref) in response to the second current, wherein the ratiometric device includes a temperature difference ratio output based on this equation:

$$\frac{\Delta T_{sens}}{\Delta T_{ref}} = \frac{T_{hot,sens} - T_{cold,sens}}{T_{hot,ref} - T_{cold,ref}};$$

and a switched-capacitor circuit having an output derived from voltages across the sensor device and the reference device, wherein the switched-capacitor circuit includes switches having a temperature mode state and a temperature difference ratio output, and a power mode state and a power difference ratio output, whereby the ratiometric device further includes a thermal conductance ratio output based on the temperature difference ratio output and the power difference ratio output.

6. A ratiometric device comprising:

a current source having a first current, a second current different from the first current, and a current-select program;

a sensor device responsive to a gas and having a sensor-cold temperature T(cold,sens) in response to the first current and a sensor-hot temperature T(hot,sens) in response to the second current;

a reference device having a reference-cold temperature T(cold,ref) in response to the first current and a reference-hot temperature T(hot,ref) in response to the second current, wherein the ratiometric device includes a temperature difference ratio output based on this equation:

$$\frac{\Delta T_{sens}}{\Delta T_{ref}} = \frac{T_{hot,sens} - T_{cold,sens}}{T_{hot,ref} - T_{cold,ref}};$$

and a switched-capacitor circuit having an output derived from voltages across the sensor device and the reference device, wherein the switched-capacitor circuit comprises
a first set of capacitors and a second set of capacitors coupled to outputs from the sensor and reference devices in a time-interleaved manner, and
a Dynamic Elements Matching module configured to resolve a mismatch between the first and second sets of capacitors.

7. The device of claim 1, wherein the sensor device is at least one of: a gas sensor, a hot wire sensor, a transducer, a resistor, an impedance, or a $CO_2$-sensitive device.

8. The device of claim 1, further comprising a thermal conductivity sensor,
    wherein the ratiometric device is embedded in the thermal conductivity sensor.

9. The device of claim 1, wherein the sensor device and reference device are made of a same material.

10. The device of claim 1, wherein the reference device is included in a sealed package separate from the sensor device.

11. The device of claim 1, further comprising a temperature compensation structure having a poly resistor and a BJT temperature sensor proximate and coupled to the poly resistor,
    wherein the temperature difference ratio output of the ratiometric device is based on outputs from the poly resistor and the BJT temperature sensor.

12. The device of claim 1, wherein the reference device is shielded from the gas.

13. The device of claim 1, wherein the reference device is at least one of:
    a device which has similar thermal properties as the sensor device;
    a thermal conductivity reference device; or
    a device which is the similar to the sensor device but having a different thermal sensitivity.

14. The device of claim 1, wherein the current source further includes a current trimming circuit configured to reduce a mismatch between the sensor device and the reference device.

15. The device of claim 1, wherein the reference device is either less responsive or more responsive to the gas than the sensor device.

16. An article of manufacture comprising at least one non-transitory, tangible machine readable storage medium containing executable machine instructions for ratiometric measurement which comprise:
    generating a first current and a second current different from the first current;
    switching between the first and second currents at a current-select program;
    measuring, from a sensor device responsive to a gas, a sensor-cold temperature T(cold,sens) in response to the first current and a sensor-hot temperature T(hot,sens) in response to the second current;
    measuring, from a reference device a reference-cold temperature T(cold,ref) in response to the first current and a reference-hot temperature T(hot,ref) in response to the second current,
    wherein the reference device is either less responsive or more responsive to the gas than the sensor device;
    calculating a temperature difference ratio based on this equation:

$$\frac{\Delta T_{sens}}{\Delta T_{ref}} = \frac{T_{hot,sens} - T_{cold,sens}}{T_{hot,ref} - T_{cold,ref}};$$

and
    generating a thermal conductivity device output signal based on the temperature difference ratio.

17. The article of manufacture of claim 16, the instructions comprising biasing the sensor device at the first current while the reference device is biased at the second current.

18. The article of manufacture of claim 16, the instructions comprising:
    reducing residual temperature dependency of the thermal conductivity device output signal by measuring the sensor device and reference device relative to a substrate poly resistor signal; and
    compensating a temperature dependency of the poly resistor with a substrate BJT temperature sensor located proximate to the poly resistor.

* * * * *